(12) United States Patent
Yalkinoglu et al.

(10) Patent No.: US 8,772,042 B2
(45) Date of Patent: Jul. 8, 2014

(54) BIOMARKERS FOR DIAGNOSING ALZHEIMER'S DISEASE

(75) Inventors: Özkan Yalkinoglu, Wuppertal (DE); Gerhard König, Newton, MA (US); Denis Francois Hochstrasser, Collonge-Bellerive (CH); Jean-Charles Sanchez, Geneva (CH); Odile Carrette, Roubaix (FR)

(73) Assignee: Bayer Intellectual Property GmbH, Monheim (DE)

( * ) Notice: Subject to any disclaimer, the term of this patent is extended or adjusted under 35 U.S.C. 154(b) by 0 days.

(21) Appl. No.: 13/099,110

(22) Filed: May 2, 2011

(65) Prior Publication Data
US 2012/0016205 A1 Jan. 19, 2012

Related U.S. Application Data

(63) Continuation of application No. 10/525,633, filed as application No. PCT/EP03/08879 on Aug. 11, 2003, now abandoned.

(30) Foreign Application Priority Data

Aug. 23, 2002 (EP) .................................. 02018283
Nov. 29, 2002 (EP) .................................. 02026643

(51) Int. Cl.
*G01N 33/00* (2006.01)
(52) U.S. Cl.
USPC ............... 436/86; 435/7.2; 435/6.16; 435/7.1
(58) Field of Classification Search
None
See application file for complete search history.

(56) References Cited

U.S. PATENT DOCUMENTS

| | | | | |
|---|---|---|---|---|
| 6,925,389 | B2 * | 8/2005 | Hitt et al. | 702/19 |
| 2004/0142388 | A1 | 7/2004 | Lamping et al. | |
| 2005/0071088 | A1 * | 3/2005 | Landfield et al. | 702/20 |
| 2005/0175626 | A1 | 8/2005 | Delacourte et al. | |
| 2009/0023145 | A1 * | 1/2009 | Nitsch et al. | 435/6 |

FOREIGN PATENT DOCUMENTS

| | | |
|---|---|---|
| WO | WO-0025138 A2 | 5/2000 |
| WO | WO-0163294 A2 | 8/2001 |

OTHER PUBLICATIONS

Davidsson et al., "Proteome analysis of cerebrospinal fluid proteins in Alzheimer patients", Clinical Neuroscience and Neuropathology (Apr. 2002), vol. 13, No. 5, pp. 611-615.*
Thakker-Varia et al., "Neuropeptides in depression: role of VGF", Behav. Brain Res. Feb. 11, 2009, 197(2), pp. 262-278.
Wei, et al., "Cystatin C: Icelandic-Like Mutation in an Animal Model of Cerebrovascular β-*Amyloidosis*," *Stroke*, 27(11): 2080-2085 (1996).
Utal, et al., "Preliminary Expression Analysis in Alzheimer's Disease Using SELDI Protein Chips," *Society for Neuroscience Abstracts*, 26 (1-2), Astract No. 83.7, 30th Annual Meeting of the Society of Neuroscience, New Orleans, LA, USA.

(Continued)

*Primary Examiner* — Dirk Bass
(74) *Attorney, Agent, or Firm* — Edwards Wildman Palmer LLP; Ralph A. Loren; Edmund J. Koundakjian

(57) ABSTRACT

A method for assessing the state of Alzheimer's disease in patients is disclosed. A method for monitoring the progression of Alzheimer's disease in patients is also disclosed. The method applies detection of specific peptide markers, e.g., using mass spectrometric analysis.

5 Claims, 1 Drawing Sheet

(56) References Cited

OTHER PUBLICATIONS

Carrette, et al., "A New Sensitive and Highly Specific Test for the Diagnosis of Alzheimer Disease Using the ProteinChip® Technology," *Database Biosis Online*, Biosciences Information Service, Philadelphia, PA, Mar. 2003. Database Accession No. PREV200300358956, Abstract and Faseb Jnl., vol. 17, No. 4-5, Mar. 2003, Abstract No. 80.3. Faseb Meeting on Experimental Biology: Translating the Genome, San Diego, CA, USA, Apr. 11-15, 2003.

* cited by examiner

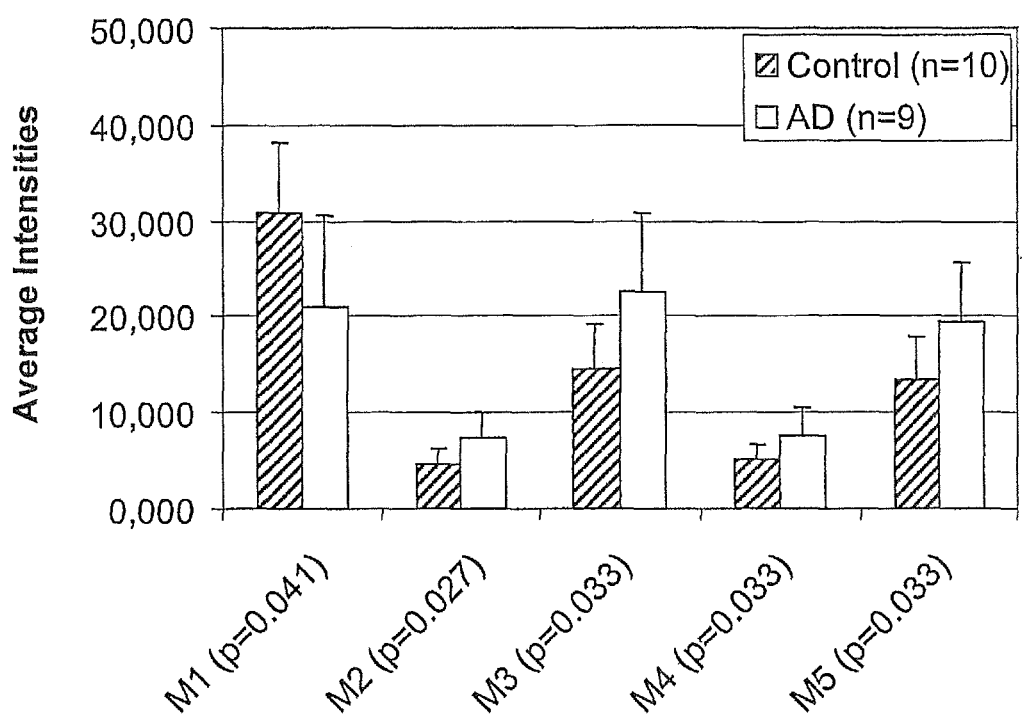

SEQUENCE LISTING

```
<160> NUMBER OF SEQ ID NOS: 17

<210> SEQ ID NO 1
<211> LENGTH: 15
<212> TYPE: PRT
<213> ORGANISM: Homo sapiens
<220> FEATURE:
<221> NAME/KEY: MISC_FEATURE
<222> LOCATION: (1)..(2)
<223> OTHER INFORMATION: Xaa = any amino acid
<220> FEATURE:
<221> NAME/KEY: MISC_FEATURE
<222> LOCATION: (5)..(5)
<223> OTHER INFORMATION: Xaa = L or I
<220> FEATURE:
<221> NAME/KEY: MISC_FEATURE
<222> LOCATION: (10)..(10)
<223> OTHER INFORMATION: Xaa = Q or K
<220> FEATURE:
<221> NAME/KEY: MISC_FEATURE
<222> LOCATION: (13)..(13)
<223> OTHER INFORMATION: Xaa = L or I
<220> FEATURE:
<221> NAME/KEY: MISC_FEATURE
<222> LOCATION: (14)..(14)
<223> OTHER INFORMATION: Xaa = L or I

<400> SEQUENCE: 1

Xaa Xaa Ala Asp Xaa Ala Gly His Gly Xaa Glu Val Xaa Xaa Arg
1               5                   10                  15

<210> SEQ ID NO 2
<211> LENGTH: 14
<212> TYPE: PRT
<213> ORGANISM: Homo sapiens
<220> FEATURE:
<221> NAME/KEY: MISC_FEATURE
<222> LOCATION: (1)..(14)
<223> OTHER INFORMATION: Xaa = L or I
<220> FEATURE:
<221> NAME/KEY: MISC_FEATURE
<222> LOCATION: (1)..(14)
<223> OTHER INFORMATION: Xaa = Leu or Ile

<400> SEQUENCE: 2

His Gly Thr Val Val Xaa Thr Ala Xaa Gly Gly Xaa Xaa Lys
1               5                   10

<210> SEQ ID NO 3
<211> LENGTH: 10
<212> TYPE: PRT
<213> ORGANISM: Homo sapiens
```

```
<400> SEQUENCE: 3

Val Asn His Val Thr Leu Ser Gln Pro Lys
1               5                   10

<210> SEQ ID NO 4
<211> LENGTH: 10
<212> TYPE: PRT
<213> ORGANISM: Homo sapiens

<400> SEQUENCE: 4

Val Glu His Ser Asp Leu Ser Phe Ser Lys
1               5                   10

<210> SEQ ID NO 5
<211> LENGTH: 13
<212> TYPE: PRT
<213> ORGANISM: Homo sapiens

<400> SEQUENCE: 5

Ile Glu Lys Val Glu His Ser Asp Leu Ser Phe Ser Lys
1               5                   10

<210> SEQ ID NO 6
<211> LENGTH: 22
<212> TYPE: PRT
<213> ORGANISM: Homo sapiens

<400> SEQUENCE: 6

Ser Asn Phe Leu Asn Cys Tyr Val Ser Gly Phe His Pro Ser Asp Ile
1               5                   10                  15

Glu Val Asp Leu Leu Lys
            20

<210> SEQ ID NO 7
<211> LENGTH: 9
<212> TYPE: PRT
<213> ORGANISM: Homo sapiens

<400> SEQUENCE: 7

Ala Ser Asn Asp Met Tyr His Ser Arg
1               5

<210> SEQ ID NO 8
<211> LENGTH: 11
<212> TYPE: PRT
<213> ORGANISM: Homo sapiens

<400> SEQUENCE: 8

Ala Leu Asp Phe Ala Val Gly Glu Tyr Asn Lys
1               5                   10

<210> SEQ ID NO 9
<211> LENGTH: 12
<212> TYPE: PRT
<213> ORGANISM: Homo sapiens

<400> SEQUENCE: 9

Arg Ala Leu Asp Phe Ala Val Gly Glu Tyr Asn Lys
1               5                   10

<210> SEQ ID NO 10
<211> LENGTH: 16
<212> TYPE: PRT
<213> ORGANISM: Homo sapiens
```

```
<400> SEQUENCE: 10

Leu Val Gly Gly Pro Met Asp Ala Ser Val Glu Glu Glu Gly Val Arg
1               5                   10                  15

<210> SEQ ID NO 11
<211> LENGTH: 16
<212> TYPE: PRT
<213> ORGANISM: Homo sapiens

<400> SEQUENCE: 11

Gln Ile Val Ala Gly Val Asn Tyr Phe Leu Asp Val Glu Leu Gly Arg
1               5                   10                  15

<210> SEQ ID NO 12
<211> LENGTH: 17
<212> TYPE: PRT
<213> ORGANISM: Homo sapiens

<400> SEQUENCE: 12

Leu Val Gly Gly Pro Met Asp Ala Ser Val Glu Glu Glu Gly Val Arg
1               5                   10                  15

Arg

<210> SEQ ID NO 13
<211> LENGTH: 17
<212> TYPE: PRT
<213> ORGANISM: Homo sapiens

<400> SEQUENCE: 13

Lys Gln Ile Val Ala Gly Val Asn Tyr Phe Leu Asp Val Glu Leu Gly
1               5                   10                  15

Arg

<210> SEQ ID NO 14
<211> LENGTH: 18
<212> TYPE: PRT
<213> ORGANISM: Homo sapiens

<400> SEQUENCE: 14

Thr Gln Pro Asn Leu Asp Asn Cys Pro Phe His Asp Gln Pro Pro His
1               5                   10                  15

Leu Lys

<210> SEQ ID NO 15
<211> LENGTH: 19
<212> TYPE: PRT
<213> ORGANISM: Homo sapiens

<400> SEQUENCE: 15

Thr Gln Pro Asn Leu Asp Asn Cys Pro Phe His Asp Gln Pro Pro His
1               5                   10                  15

Leu Lys Arg

<210> SEQ ID NO 16
<211> LENGTH: 24
<212> TYPE: PRT
<213> ORGANISM: Homo sapiens

<400> SEQUENCE: 16

Ser Ser Pro Gly Lys Pro Pro Arg Leu Val Gly Gly Pro Met Asp Ala
1               5                   10                  15
```

```
Ser Val Glu Glu Glu Gly Val Arg
            20

<210> SEQ ID NO 17
<211> LENGTH: 20
<212> TYPE: PRT
<213> ORGANISM: Homo sapiens

<400> SEQUENCE: 17

Val Gly Glu Glu Asp Glu Glu Ala Ala Glu Ala Glu Ala Glu Ala Glu
1               5                   10                  15

Glu Ala Glu Arg
            20
```

BIOMARKERS FOR DIAGNOSING ALZHEIMER'S DISEASE

FIELD OF THE INVENTION

The invention is in the field of diagnostics. More specifically, the invention is in the field of assessing the state of Alzheimer's disease in subjects by detection of Alzheimer's disease-specific marker polypeptides.

BACKGROUND OF THE INVENTION

Alzheimer's Disease

Alzheimer's disease is an increasingly prevalent form of neurodegeneration that accounts for approximately 50-60% of the overall cases of dementia among people over 65 years of age. Pathologically, Alzheimer's disease neurodegeneration is characterised by prominent atrophy of corticolimbic structures with neuronal death and loss of neuronal synapses, neurofibrillary tangle (NFT) formation, and the formation of senile plaques containing deposits of amyloid β1-42 (Aβ42) aggregates in the brain [Francis P T 1999]. The duration of the progressive cognitive decline is approximately 7 years from the occurrence of first signs until death. It is assumed that the clinical phase is preceded by a 15-30 years preclinical period of continuous deposition of amyloid plaques and neurofibrillary tangles. Age of onset and progression of the disease are largely determined by causative gene mutations and by genetic susceptibility factors. Several environmental risk factors may add to the individual genetic risk factors. Genetic factors known to be involved in the familial form of Alzheimer's disease with early onset of the disease are: mutations in presenilin 1 (PS1), presenilin 2 (PS2), and amyloid precursor protein (APP) genes, and the presence of the apolipoprotein E4 allele. However, the majority (95%) of Alzheimer's disease cases is sporadic and heterogeneous.

Currently, clinical diagnosis of Alzheimer's disease can only be established at later stages of the disease, when cognitive perfotniance is significantly decreased and paralleled by structural alterations of the brain. The clinical diagnostic work up requires a careful medical history; physical and neurological examination; blood, urine and cerebrospinal fluid (CSF) examinations to exclude metabolic and medical disease states that might masquerade Alzheimer's disease; detailed psychometric examinations to assess mental status and cognitive performance, and imaging techniques such as computed tomographic scan or magnetic resonance imaging of the brain. Diagnostic evaluations at expert centres reach an accuracy of about 80-85%. Due to the fact that these tests are expensive and time consuming, and are particularly inconvenient to patients, there is an increasing need for easy-accessible specific diagnostic biomolecule markers, which can be measured in body fluids, such as CSF, blood or urine, and which have a high positive predictive value for diagnosis of Alzheimer's disease, or would help to distinguish Alzheimer's disease from other forms of dementia. Furthermore, reliable markers sensitive to disease progression may constitute surrogate parameters, a major prerequisite for the evaluation and development of new causal oriented and disease modifying therapeutic strategies in Alzheimer's disease.

Since CSF directly surrounds the brain, changes in its protein composition may most accurately reflect pathologic conditions that are associated with specific alterations of the protein expression patterns. Over the last decade, a number of biological abnormalities have been reported in the cerebrospinal fluid (CSF) of Alzheimer's disease patients, in particular altered levels of the Aβ1-42 fragment of the amyloid precursor protein, and altered levels of the hyperphosphorylated tau protein. The sensitivity and specificity of these markers, however, is low or only modest [The Ronald and Nancy Reagan Research Institue of the Alzheimer's Association and the National Institute on Aging Working Group, 1998, Robles A 1998, Termissen C E et al., 2002].

Hence, there is a need for novel biomarkers with sufficient sensitivity and specificity for (i) detecting Alzheimer's disease as early as possible, and (ii) to allow disease differentiation from other types of dementia or neurodegenerative diseases, and (iii) monitoring therapeutic efficacy as surrogate parameter, e.g. in clinical drug development, and to initiate pharmacotherapy as early as possible and postpone loss of memory and disease progression.

Protein Chip Technology

A Protein chip technology called Surface Enhanced Laser Desorption/Ionisation time of flight mass spectrometry (SELDI-TOF MS) has recently been developed to facilitate protein profiling of complex biological mixtures [Davies H A 2000, Fung E T 2001, Merchant M 2000].

Protein chip mass spectrometry has already been used by several groups to detect potentially novel biomarkers of prostate and bladder [Adam B L 2001] or breast cancer [Wulfkuhle J D 2001] in serum, seminal plasma, nipple fluid, urine or cell extracts. For a review on biomarker search using SELDI-TOF MS, see [Issaq H J 2002].

Cystatin C

Initially described in 1961 in cerebrospinal fluid (CSF), cystatin C (γ trace or post-γ globulin, Acc. No. P01034) is a small cystein proteinase inhibitor present in all human body fluids at physiologically relevant concentrations. The physiological role of cystatin C is likely to regulate extracellular cysteine protease activity, which results from microbial invasion or release of lysosomal proteinases from dying or diseased cells. Cystatin C colocalises with β-amyloid (Aβ) within the arteriolar walls in Alzheimer's disease brains and cerebral amyloid angiopathy [Levy E 2001]. There are two common haplotypes of the CST3 gene coding for cystatin C (A and B) that differ from each other at three sites: two single base pair changes in the promoter region and one in the signal peptide domain that causes an amino acid substitution (alanine to threonine). Recently, case control studies found associations of CST3 with increased risk for late onset Alzheimer's disease [Crawford F C 2000, Finckh U 2000, Beyer K 2001].

Hereditary cerebral hemorrhage with amyloidosis, Icelandic type (HCHWA-I), also called hereditary cystatin C amyloid angiopathy (HCCAA), is an autosomal dominant form of cerebral amyloid angiopathy (CAA). The amyloid deposited in the brain vessel's walls is composed mainly of a variant of cystatin C characterised by the presence of the Leu68-Gln substitution [Cohen 1983, Ghiso 1986]. This pathology is also coupled to a decreased concentration of this major cystein proteinase inhibitor in cerebrospinal fluid and leads to its amyloid deposition in the brain [Grubb A O 1984].

Leung-Tack et al have also purified two N-terminal truncated isoforms of cystatin C in urine from one patient who had received renal transplant. According to their data, (des1-4) cystatin C has an inhibiting effect on two functions of human peripheral mononuclear cells (PMN): $O_2^-$ release and phagocytosis, which may be due to the N-terminal sequence 'KPPR'. Their data support a potentially important role for cystatin C as a possible immunomodulator during inflammation. Accumulating evidence indicates that increased free radical mediated damage to cellular function contributes to the ageing process and age-related neurodegenerative disorders. Oxidative stress may play a role in Alzheimer's disease, Parkinson's disease, amyotrophic lateral sclerosis (ALS). Although free-radical damage to neurons may not be the primary event initiating these diseases, it appears that free-radical damage is involved in the pathogenetic cascade of these disorders.

Beta-2-Microglobulin

Beta-2-microglobulin (Ace. No. P01884) constitutes the small constant component of the class I major histocompatibility complex (CMH) and its presence in biological fluids represents the balance between membrane protein turnover and elimination. Since this peptide seems to be increased in some diseases characterised by an elevation of the immune response, its quantification in body fluids has become a useful index of immunological state in vivo [Hoekman et al 1985]. The function of this protein is unclear, but it seems to be implicated in diseases, which involve glial cell destruction [Ernrudh et al 1987].

The technical problem which is solved by the present invention is the provision of improved methods for diagnosing Alzheimer's disease and/or monitoring the progression of Alzheimer's disease in a subject.

Neurosecretary Protein (VGF)

VGF (human VGF, Acc.-No.: O15240) is a secretory peptide precursor that is expressed and processed by neuronal cells [Canu et al. 1997]. In situ hybridization studies in the adult rat central nervous system have revealed that the VGF mRNA is widely distributed throughout the brain with prominent expression in the hippocampus, entorhinal cortex, and neocortex. Furthermore, it has been shown that VGF transcription and secretion is selectively upregulated by neurotrophins like NGF and BDNF, and by depolarization in vitro. Increased BDNF expression can be observed in dentate gyrus and CA3 regions of the hippocampus, which are tissues that appear to die early in Alzheimer Disease pathogenesis.

DESCRIPTION OF THE INVENTION

The invention is based on the surprising finding that specific polypeptides are differentially expressed in subjects having Alzheimer's disease when compared to a healthy control group. These differentially expressed polypeptides can be, e.g., detected in samples of cerebrospinal fluid of the subject in which Alzheimer's disease is to be diagnosed. The individual polypeptides of the invention can be detected and/or quantified alone or in combination with other polypeptides of the invention. The polypeptide markers of the invention are defined by their respective molecular weight. Five markers identified by the SAX2 method as described in the Examples show the following molecular masses:

Marker 1 (M1): 4824±20 Da;
Marker 2 (M2): 7691±20 Da;
Marker 3 (M3): 11787±20 Da;
Marker 4 (M4): 11988±20 Da;
Marker 5 (M5): 13416±20 Da.

Table one shows the observed molecular weight of polypeptide markers M1 to M5 as determined by SELDI-TOF MS, the amino acid sequences of observed fragments of polypeptide markers M1 to M5, and the protein from which the polypeptide markers M1 to M5 originate.

TABLE 1

| Marker | SELDI observed MW | Amino Acid Sequence | Protein Name |
|---|---|---|---|
| M1 | 4823.5 Da ± 1.7 | VGEEDEEAAEAEAEAEEAER<br>SEQ ID NO: 17 | VGF4.8 |
| M2 | 7691.4 Da ± 4.9 | XXAD(L/I)AGHG(Q/K)EV(L/I)(L/I)R<br>SEQ ID NO: 1 | Human myoglobin new variant |
|  |  | HGTVV(L/I)TA(L/I)GG(L/I)(L/I)K<br>SEQ ID NO: 2 |  |
| M3 | 11786.9 Da ± 7.6 | VNHVTLSQPK<br>SEQ ID NO: 3 | Human beta-2-microglobulin |
| M4 | 11988.4 Da ± 5.9 | VEHSDLSFSK<br>SEQ ID NO: 4 |  |
|  |  | IEKVEESDLSFSK<br>SEQ ID NO: 5 |  |
|  |  | SNFLNCYVSGFHPSDIEVDLLK<br>SEQ ID NO: 6 |  |
| M5 | 13416.4 Da ± 9.4 | ASNDMYHSR<br>SEQ ID NO: 7 | human Cystatin C |
|  |  | ALDFAVGEYNK<br>SEQ ID NO: 8 |  |
|  |  | RALDFAVGEYNK<br>SEQ ID NO: 9 |  |
|  |  | LVGGPMDASVEEEGVR<br>SEQ ID NO: 10 |  |
|  |  | QIVAGVNYFLDVELGR<br>SEQ ID NO: 11 |  |
|  |  | LVGGPMDASVEREGVRR<br>SEQ ID NO: 12 |  |

TABLE 1-continued

| Marker SELDI observed MW | Amino Acid Sequence | Protein Name |
| --- | --- | --- |
| | KQIVAGVNYFLDVELGR<br>SEQ ID NO: 13 | |
| | TQPNLDNCPFHDQPPHLK<br>SEQ ID NO: 14 | |
| | TQPNLDNCPFHDQPPHLKR<br>SEQ ID NO: 15 | |
| | SSPGKPPRLVGGPMDASVEEEGVR<br>SEQ ID NO: 16 | |

The differentially expressed polypeptides of the invention can be, e.g., detected in samples of cerebrospinal fluid of the subject in which Alzheimer's disease is to be diagnosed. In addition, depending on the specific embodiment, the source of samples to measure the abundance of the polypeptide markers of the invention, can also be blood, serum, or urine, but is not limited to these body compartments.

As shown in FIG. 1, compared to a negative diagnosis (healthy controls), M1 is under-expressed in the CSF of Alzheimer's disease patients ($p<0.05$), while the markers M2 to M5 are over-expressed in CSF of Alzheimer's disease patients ($p<0.05$).

An altered level of one or several polypeptides of the invention, compared to the level of polypeptides of the invention in healthy control subjects, will allow assessing the state of and/or monitoring the progression of Alzheimer's disease in a subject, will allow monitoring the effectiveness of Alzheimer's disease treatment, and will be useful information for drug development. Furthermore, these biomolecule markers are useful for differentiating Alzheimer's disease from other forms of dementia and neurodegenerative disorders.

Preferred subjects in which Alzheimer's disease is to be diagnosed or monitored are human subjects. However, diagnosis of Alzheimer's disease according to the invention is also possible with other mammals. If necessary, orthologues of the peptide markers of the invention can be used.

The invention also relates to the use of mass spectrometry (MS) for detecting Alzheimer's disease in human subjects and for assessing the progression of Alzheimer's disease in human subjects by detecting and/or quantifying the amount of specific polypeptides in samples drawn from the subject's body fluids. In a preferred embodiment of the invention, the sample is drawn from the subject's cerebrospinal fluid (CSF).

Detection and/or quantification of the polypeptides of the invention is preferably achieved by quantifying the signal which is detected by MS at specific molecular mass to charge ratios (M/z) which correspond to the M/z ratios of the polypeptides of the invention. Preferably, M/z ratios close to the one of the polypeptides of the invention are also measured.

Detection and/or quantification of the polypeptides of the invention can also be achieved by using an immunoassay using specific antibodies raised against the specified marker(s) or polypeptide fragments thereof. Antibodies can be prepared by using the purified marker(s) or fragments thereof, or using synthetic or recombinantly expressed polypeptide(s) consisting of the specific amino acid sequence of the marker(s) using any suitable method known in the art [Coligan 1991]. Such techniques include, but are not limited to, antibody preparation by selection of antibodies from libraries of recombinant antibodies in phage or appropriate vectors, as well as preparation of polyclonal and monoclonal antibodies by immunising rabbits or mice [Huse 1989, Ward 1989]. After the antibody is provided, a marker can be detected and/or quantified using any of a number of standard immunological binding assays [U.S. Pat. Nos. 4,366,241; 4,376,110; 4,517,288; and 4,837,168]. Useful assays include, but are not limited to, for example, an enzyme immune assay (EIA) such as enzyme-linked immunosorbent assay (ELISA), a radioimmune assay (RIA), a Western blot assay, or a slot or dot blot assay. For a review of the general immunoassays see [Coligan 1991]. Generally, a sample obtained from a subject can be contacted with the antibody that specifically binds the marker. A powerful technique to capture the specified marker(s) from a complex body fluid sample is to use the antibody fixed to solid supports, such as glass or plastic, e.g. microliter plate, a stick, a bead, or microbead. Alternatively, marker(s) can also be captured from the body fluid sample by the specific antibody immobilised to a probe substrate or a ProteinChip™ array, as described for the SELDI-based immunoassay [Xiao 2001]. After incubating the sample with antibodies, the non-bound material is washed under specified conditions and the antibody-marker complex formed can be detected, using appropriate detection reagents. In an embodiment using the SELDI ProteinChip™ array technique the marker(s) selectively enriched by the immobilised antibody can be detected and quantified by matrix-assisted laser desorption ionisation mass spectrometry.

The invention specifically relates to 1. a method of assessing the state of Alzheimer's disease in a subject comprising detection of at least one polypeptide comprised in a group of polypeptides consisting of
   i) a polypeptide having a molecular mass of 4824±20 Da,
   ii) a polypeptide having a molecular mass of 7691±20 Da,
   iii) a polypeptide having a molecular mass of 11787±20 Da,
   iv) a polypeptide having a molecular mass of 11988±20 Da, and
   v) a polypeptide having a molecular mass of 13416±20 Da.
   The invention further relates to a method of assessing the state of Alzheimer's disease in a subject comprising detection of at least one polypeptide comprised in a group of polypeptides having, respectively, molecular masses of 4824±20 Da, of 7691±20 Da, of 11787±20 Da, of 11988±20 Da, of 13416±20 Da, of 4769±20 Da, of 6958±20 Da, of 6991±20 Da, of 13412±20 Da, of 13787±20 Da, of 17276±20 Da, of 40437±20 Da, of 6895±20 Da, of 6928±20 Da, of 7691±20 Da, of 7769±20 Da, of 7934±20 Da, of 5082±20 Da, of 6267±20 Da, of 6518±20 Da, of 7274±20 Da, and of 8209±20 Da.

Whereas detection of one such polypeptide is in most cases sufficient to reliably diagnose Alzheimer's disease, detection of two or more polypeptides of the invention can increase the sensitivity and robustness of the method. Preferably, 1, 2, 3, 4, 5, 10, and, most preferred, all of said polypeptides will be detected from the same sample. The detection can also be carried out simultaneously with the detection of other polypeptides which are preferably also differentially expressed in subjects having Alzheimer's disease as compared to healthy subjects. "Assessing the state of Alzheimer's disease" shall be understood as diagnosing the presence of Alzheimer's disease in a subject or a patient, as assessing the progression of the disease in a subject or a patient, and/or as assessing the proneness of a subject to develop Alzheimer's disease.

2. The invention further relates to the method of point 1 in which 2, or 3, or 4, or 5 polypeptides of said group of peptides are detected. The invention further relates to a method of point 1 in which 2, or 3, or 4, or 5, or 10 or all polypeptides of said group of peptides are detected.

3. The invention further relates to a method of assessing the state of Alzheimer's disease in a subject comprising detection of at least one polypeptide comprising the sequence of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, and/or SEQ ID NO:16. The invention further relates to a method of assessing the state of Alzheimer's disease in a subject comprising detection of at least one polypeptide comprising the sequence of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, and/or SEQ ID NO:17. Whereas detection of one such polypeptide is in most cases sufficient to reliably diagnose Alzheimer's disease, detection of two or more polypeptides of the invention can increase the sensitivity and robustness of the method. Preferably, 1, 2, 3, 4, 5, 10, or all of said polypeptides will be detected from the same sample. The detection can also be carried out simultaneously with the detection of other polypeptides which are preferably also differentially expressed in subjects having Alzheimer's disease as compared to healthy subjects.

4. The invention further relates to a method of assessing the state of Alzheimer's disease in a subject comprising detection of at least one polypeptide comprised in a group of polypeptides consisting of
   i) human cystatin C,
   ii) human beta-2-microglobulin,
   iii) human myoglobin (new variant),
   iv) a fragment of at least 5, 8, 10, or 20 amino acids of human cystatin C,
   v) a fragment of at least 5, 8, 10, or 20 amino acids of human beta-2-microglobulin, and
   vi) a fragment of at least 5, 8, 10, or 20 amino acids of human myoglobin (new variant).

The invention further relates to a method of assessing the state of Alzheimer's disease in a subject comprising detection of at least one polypeptide comprised in a group of polypeptides consisting of
   i) human cystatin C,
   ii) human beta-2-microglobulin,
   iii) human myoglobin (new variant),
   iv) human neurosecretory protein VGF,
   v) a fragment of at least 5, 8, 10, or 20 amino acids of human cystatin C,
   vi) a fragment of at least 5, 8, 10, or 20 amino acids of human beta-2-microglobulin,
   vii) a fragment of at least 5, 8, 10, or 20 amino acids of human myoglobin (new variant), and
   viii) a fragment of at least 5, 8, 10, or 20 amino acids of neurosecretory protein VGF.

Whereas detection of one such polypeptide is in most cases sufficient to reliably diagnose Alzheimer's disease, detection of two or more of said polypeptides can increase the sensitivity and robustness of the method. Preferably, 1, 2, 3, 4, 5, or 6 of said polypeptides will be detected from the same sample. More preferably, 1, 2, 3, 4, 5, 6 or all of said polypeptides will be detected from the same sample. The detection can also be carried out simultaneously with the detection of other polypeptides which are preferably also differentially expressed in subjects having Alzheimer's disease as compared to healthy subjects.

5. The invention further relates to a method of investigating the progression of Alzheimer's disease in a subject characterised in that a method of any of points 1 to 4 is performed with at least two distinct samples drawn from the same subject. For this purpose, samples drawn from a subject at different points in time will be analysed. Changes in the amount of the respective polypeptide(s) will allow to draw conclusions on the progression of Alzheimer's disease in the subject.

6. The invention further relates to a method of any of points 1 to 5, wherein detection of said polypeptide(s) is by SELDI-TOF MS. Other suitable mass spectrometric methods and other methods of detection can alternatively be used. More specifically, the invention relates to a method of any of points 1 to 5, wherein detection of said polypeptide(s) is by SELDI-TOF MS in which the hydrophobic H50, the WCX2, or the IMAC surface is used as a support upon ionisation. Different supports for ionisation yield different sensitivity for specific proteins of interest.

7. The invention further relates to a method of any of points 1 to 5, wherein specific antibodies or antibodies recognising said polypeptide(s) are used for detection of said polypeptide(s).

8. The invention further relates to a method of any of points 1 to 7, wherein detection is in a sample comprising CSF of said patient. A sample drawn from a subject can be processed immediately after it has been taken, or it can first be frozen and be analysed later. Samples may also consist of or contain other body fluids such as blood, serum, plasma, urine, seminal plasma, nipple fluid, or cell extracts.

9. The invention further relates to a kit comprising a polypeptide having a molecular mass of 4824±20 Da, a polypeptide having a molecular mass of 7691±20 Da, a polypeptide having a molecular mass of 11787 d 20 Da, a polypeptide having a molecular mass of 11988 d 20 Da, and/or a polypeptide having a molecular mass of 13416±20 Da. The invention further relates to a kit comprising a polypeptide having a molecular mass of 4824±20 Da, a polypeptide having a molecular mass of 7691±20 Da, a polypeptide having a molecular mass of 11787±20 Da, a polypeptide having a molecular mass of 11988±20 Da, and a polypeptide having a molecular mass of 13416±20 Da. The invention further relates to a kit comprising polypeptides having a molecular mass of 4824±±20 Da, of 7691±20 Da, of 11787±20 Da, of 11988±20 Da, of 13416±20 Da, of 4769±20 Da, of 6958±20 Da, of 6991±20 Da, of 13412±20 Da, of 13787±20 Da, of 17276±20 Da, of 40437±20 Da, of 6895±20 Da, of 6928±20 Da, of 7691±20 Da, of 7769±20 Da, of 7934±20 Da, of 5082±20 Da, of 6267±20 Da, of 6518±20 Da, of 7274±20 Da, and/or of 8209±20 Da. Such a kit can be applied for various purposes, e.g., for use as a standard in one of the above mentioned methods. Said kit can comprise 2, 5, 10, or all of the above polypeptides.

10. The invention further relates to a kit comprising a fragment of at least 5 amino acids of human cystatin C, a fragment of at least 5 amino acids of human beta-2-microglobulin, and a fragment of at least 5 amino acids of human myoglobin. This kit can be applied for various purposes, e.g., for use as a standard in one of the above mentioned methods. The invention further relates to a kit comprising a fragment of at least 5, 10 or 20 amino acids of human cystatin C, a fragment of at least 5, 10 or 20 amino acids of human beta-2-microglobulin, a fragment of at least 5, 10 or 20 amino acids of human myoglobin, and a fragment of at least 5, 10 or 20 amino acids of neurosecretory protein VGF. These kits can be applied for various purposes, e.g., for use as a standard in one of the above mentioned methods.

BRIEF DESCRIPTION OF THE FIGURES

FIG. 1:
Average intensities of the five marker peptides of Table 1, which are differentially expressed in the diseased group when compared to the control groups.

EXAMPLES

The invention is further described by one or several of the following examples. These examples are not to be understood as restricting the scope of the invention to the examples by any means.

Example 1

Patients Evaluation and CSF Sampling

Diagnosis of Alzheimer's disease in human subjects was made according to criteria of the National Institute of Neurologic and Communicative Disorders and Stroke-Alzheimer's disease and Related Disorders Association (NINCDS-ADRDA). The Alzheimer's disease group consisted of 9 patients aged 75±7 years, six men and three women. The group of healthy control subjects consisted of 10 individuals aged 78±14 years, two men and eight women with no history, symptoms or signs of psychiatric or neurological disease.

Informed consent was given by each patient and the patients' caregivers before the investigation. The study was approved by the local ethics committee. After lumbar puncture, CSF samples were frozen on dry ice immediately upon withdrawal at the bedside in 0.5 ml aliquots and stored at −80° C. until analyses.

Example 2

ProteinChip SELDI Analysis of CSF on SAX2 Chip

SAX 2 Proteinchip array (Ciphergen Biosystems, Fremont, Calif., USA) were equilibrated for 5 min with 5 µl of binding buffer (100 mM Na Acetate pH=4.0). The buffer was carefully removed with an handkerchief and 2.5 µl of binding buffer was added to the wells. Crude CSF samples (2.5 µl) were added to the wells and incubated for 20 min at room temperature in a humidity chamber on a rocking platform. CSF was removed and the wells were individually washed with 10 µl of binding buffer for 5 min. The arrays were then placed in a 15 ml conical Eppendorf and washed twice with the binding buffer for 5 min. Finally, the chip was rinsed twice with distilled water. Excess of $H_2O$ was removed and while the surface was still moist, two additions per well of 0.5 µl of sinapinic acid (SPA) (2 mg/ml) in 50% (vol/vol) acetonitrile and 0.5% (vol/vol) trifluoroacetic acid was performed and dried. The arrays were then read in a ProteinChip reader system, PBS II series (Ciphergen Biosystems). The laser beam was focused on the sample in vacuo. This caused the proteins absorbed to the matrix to become ionised and, simultaneously to be desorbed from the Proteinchip array surface. The ionised proteins were detected and their molecular masses were determined according to their time-of-flight (TOF). TOF mass spectra, collected in the positive ion mode were generated using an average of 65 laser shots throughout the spot at a laser power set slightly above threshold (10-15% higher than the threshold) High mass to acquire was set at 40 kDa, optimised from 1 to 15 kDa. Spectra were collected and analysed using the Ciphergen Proteinchip (version 3.0) software. External calibration of the reader was performed using the "all-in-1" peptide molecular weight standards (Ciphergen biosystems, Inc.) diluted in the SPA matrix (1:1, vol/vol) and directly applied onto a well. Protein profile comparison was performed after nor realisation on total ion current of all the spectra included in the same experiment. The reproducibility was tested by analysing different aliquots of the same CSF sample on 4 different wells of the same proteinchip array (intraassay intrachip reproducibility), on two different chips (intraassay interchip reproducibility) processed in parallel, and reproduced in an other experiment (interassay reproducibility).

Analysis of CSF samples from 9 patients diagnosed with Alzheimer's disease relative to 10 controls revealed that 5 peaks were significantly differentially expressed between the two groups (p<0.05). The approximate average SELDI mass associated with the five differentially expressed proteins was 4.82 kDa, 7.7 kDa, 11.8 kDa and 12.0 kDa and 13.4 kDa (p<0.05) (see Table 1, FIG. 1).

Example 3

Strong Anionic Exchange Chromatography (SAX) Purification

In order to identify the proteins corresponding to these peaks, a fractionation of crude CSF on a SAX spin column was performed. The eluted fractions were analysed by SELDI-TOF MS.

SAX spin column, lot number SAX2-001116-01, (Ciphergen Biosystems, Fremont, Calif., USA) was rehydrated overnight at 4° C. in the equilibration buffer (20 mM tris(hydroxymethyl)aminomethane hydrochloride (Tris-HCl), 5 mM NaCl, pH 9.0). The column was warmed up at room temperature and air bubbles were removed. The equilibration buffer was let flow through column matrix by gravity. Equilibration buffer (0.5 ml) was added to the column and passed through the resin twice. Two ml of control CSF was diluted in the equilibration buffer (1:1, vol/vol). Protein sample was loaded to the column by fraction of 0.8 ml and allowed to run through the column by gravity until no drops came out of the column. The column was then centrifuged at 150×g for 1 min. The resin was then washed with an equivalent volume of equilibration buffer. This step was repeated several times in order to load the whole sample onto the resin. Elution of the bound proteins was performed by decreasing the pH. Elution buffer A consisted of 20 mM Tris-HCl, 5 mM NaCl pH 8.0; elution buffer B=20 mM sodium phosphate pH 7.0; elution buffer C=20 mM sodium phosphate pH 6.0; elution buffer D=20 mM sodium phosphate and citrate pH 5.0; elution buffer E=20 mM sodium phosphate and citrate pH 4.0; elution buffer F=20 mM sodium phosphate and citrate pH 3.4; elution buffer G=30% acetonitrile in elution buffer F. Elution was performed by applying 2×75 µl of the elution buffer and centrifugation at 150×g for 1 min. Each collected fraction (150 µl) was concentrated on a speed-vac to a volume of 104 µl. Protein profiles were analysed on SELDI-TOF MS using SAX 2 Proteinchip arrays. The chip was equilibrated with a binding buffer consisting of 20 mM Tris-HCl, 5 mM NaCl, pH=9.0. An aliquot of 0.5 µl of each concentrated fraction was applied directly onto 2.5 µl of binding buffer per spot and processed as previously described. The rest of the fractions were loaded onto a Tris tricine gel as described below.

The differentially expressed peak of 13.4 kDa was eluted with buffer A (20 mM Tris-HCl 5 mM NaCl pH 8.0) and B (20 mM sodium phosphate pH 7.0). The differentially expressed peaks of 11.8 kDa and 12.0 kDa were found in the fraction eluted with buffer C (20 mM sodium phosphate pH 6.0) and D (20 mM sodium phosphate and citrate pH 5.0). The cluster of 7.7 kDa was eluted with buffer D (20 mM sodium phosphate and citrate pH 5.0) and E (20 mM sodium phosphate and citrate pH 4.0).

Each eluted fraction was loaded on a 16.5% Tris Tricine sodium dodecyl sulfate polyacrylamide gel and electrophoresed (SDS PAGE). After coloration with coomassie blue, the bands seen on the gel confirmed the results obtained by SELDI analysis. The band corresponding to the cluster of 7.7 kDa, 11.8 kDa and 12.0 kDa were cut out. Proteins were extracted as described in Example 6 and identified by Q-TOF. The 7.7 kDa peak MS analysis did not match with any known human protein, however, may indicate to a new variant or homologue of myoglobin. Peptide sequences were the following:

```
XXAD(L/I)AGHG(Q/K)EV(L/I)(L/I)R    SEQ ID NO: 1
and

HGTVV(L/I)TA(L/I)GG(L/I)(L/I)K     SEQ ID NO: 2.
```

The MS analysis of the 11.8 kDa and 12.0 kDa peaks identified beta-2-microglobulin for both of them.

Since the cluster of 13.4 kDa could not be seen on the Tris Tricine gel, a Tris glycine SDS-PAGE electrophoresis was performed on crude CSF samples. The band corresponding to the beta-2-microglobulin could be easily found on this stained gel. We concluded that the protein migrating just above the beta-2-microglobulin could correspond to the next abundant protein seen on the SELDI profile, namely the 13.4 kDa peak. The band was excised from the gel and digested by trypsin before MALDI analysis. The peptide mass fingerprint analysis allowed to identify the Cystatin C. The sequence coverage provided by the analysis was 60%.

Example 4

Monodimensional Electrophoresis/Tris Glycine Gels

Twenty µl of CSF were mixed with 10 µl of denaturing Laemmli buffer [Laemmli 1970]. The samples were heated to 95° C. for 5 min, and loaded on a 15% T (T=total acrylamide concentration) SDS-polyacrylamide gel according to the method of Laemmli. Gels were stained in a solution containing Coomassie Brilliant Blue R-250 (0.1% w/v) and methanol (50% v/v) for 30 min. Destaining was done in a solution containing methanol (40% v/v) and acetic acid (10% v/v).

Example 5

Monodimensional Electrophoresis: Tris Tricine Gels

Tris tricine SDS-PAGE electrophoresis was performed according to Schagger and von Sagow [1987] using precast 16.5% T gels (Biorad, Hercules, Calif.). The anode buffer consisted of 0.2M Tris-HCl, pH 8.9 and the cathode buffer consisted of 0.1M Tris-HCl, 0.1M Tricine, 0.1% SDS, pH 8.25. Samples were diluted in 10 µl of 50 mM Tris-HCl, 4% (w/v) SDS 12% (w/v) sucrose, 5% (v/v) β morcaptoethanol, and trace of bromophenol blue, pH 6.8. After denaturation at 95° C. for 5 min, samples were loaded onto the gel. Gels were run at 80V for 3 hours. After electrophoresis, gels were fixed in 40% methanol, 10% acetic acid for 30 min. Gels were then stained with Colloidal blue coomassie G250 overnight and destained in 30% methanol. Bands to be identified were immediately cut, placed in an eppendorf and kept at 4° C. until further analysis. The apparent molecular masses were determined by running polypeptide molecular weight (MW) standards: Triosephophate isomerase MW 26,625; Myoglobin MW 16,950; α-lactalbumin MW 14,437; Aprotinin MW 6,512; Insulin b chain, oxidised MW 3,496 and Bacitracin MW 1,423 (Biorad).

Example 6

Protein Digestion and Peptide Extraction [Bienvenu 1999]

Fragments of gels containing proteins of interest were cut out for digestion of the proteins with trypsin using previous published procedures [Shevche 1996, Hellman 1994, Rosenfeld 1992] and modified as described below. The piece of gel was first destained with 100 µl of 50 mM ammonium bicarbonate, 30% (v/v) acetonitrile during 15 min at room temperature. Destaining solution was removed and replaced by 25 µl of 10 mM DL-dithiothreitol (DTT) in 50 mM ammonium bicarbonate and incubated 35 min at 56° C. DTT solution was then replaced by 25 of 55 mM iodoacetamide in 50 mM ammonium bicarbonate and incubated during 45 min at room temperature in the dark. Gel pieces were washed for 10 min with 100 µl of 50 mM ammonium bicarbonate and for 10 min with 100 µl of 50 mM ammonium bicarbonate and 30% (v/v) acetonitrile.

Gel pieces were then dried for 30 min in a Hetovac vacuum centrifuge (HETO, Allerod, Denmark). Dried pieces of gel were rehydrated for 45 mM at 4° C. in 5-20 µl of a solution of 50 mM ammonium bicarbonate containing trypsin at 6.25 ng/µl. After an over-night incubation at 37° C., gel pieces were dried under high vacuum centrifuge before being rehydrated by the addition of 20 µl of distilled water and finally dried again in a speed-vac for 30 min. Extraction of the peptides was performed with 20 µl of 0.1% (v/v) trifluoroacetic acid (TFA) for 20 min at room temperature with occasional shaking. The TFA solution containing the peptides was transferred to a polypropylene tube. A second elution was performed with 20 µl of 0.1% (v/v) TFA in 50% (v/v) acetonitrile for 20 min at room temperature with occasional shaking. The second TFA solution was pooled with the first one. The volume of the pooled extracts was reduced to 1-2 µl by evaporation under vacuum. Control extractions (blanks) were performed using pieces of gels devoid of proteins.

Example 7

Protein Identification by Peptide Mass Fingerprinting Analysis 1.5 µl of sample was placed on a MALDI 100-well target plate. Same volumes of matrix (10 mg/ml co-Cyano-4-hydroxycinnamic acid in 50% (v/v) acetonitrile, 0.1% (v/v) TFA) were added to the previously loaded digest. Samples were dried as quickly as possible using a vacuum container. Mass measurement from liquid solution were conducted with a MALDI-TOF mass spectrometer Voyager™ Elite and Super STR (PerSeptive Biosystems, Framingham Mass., USA) equipped with a 337 nm nitrogen laser. The analyser was used in the reflectron mode at an accelerating voltage of 20 kV, a delayed extraction parameter of 100-140 ns and a low mass gate of 850 Da. Laser power was set slightly above threshold (10-15% higher than the threshold) for molecular ion production. Spectra were obtained by summation of 10 to 256 consecutive laser shots. Masses of the 60 highest peaks were extracted from the spectra and used for protein identification using the SmartIdent peptide mass fingerprint tool [Gras 1999]. The research was conducted against SWISS-PROT and TrEMBL databases. The query was made for the human, the minimum number of matched masses was 4, the maximal tolerance for masses was 50 ppm after an internal calibration using autolysis product of trypsin, at most one missed cleavage for tryptic peptides was allowed, and the modifications accepted were carboxymethylation with iodoacetamide of cysteines and artefactual oxidation of methionines.

Example 8

Protein Identification by Peptide Fragmentation Analysis

Prior to nanoLC (LC=liquid chromatography) separation, the volumes of peptide containing solutions were adjusted to 7 µl by addition of a 0.1% (v/v) formic acid solution. Samples were settled in a Triathlon autosampler (Spack, Emmen, Holland). For each experiment, 5 µl of peptide containing solution were injected on a C18 reverse phase column of 75 µm inner diameter (YMS-ODS-AQ200, Michrom Bioresource, Auburn, Calif.). Peptides were eluted with an acetonitrile (ACN) gradient in the presence of 0.1% (v/v) formic acid, using SunFlow pumps. (SunChrom, Friderichsdorf, Germany). A flow splitter was used in order to decrease the flow rate after the pumps from 200 to 0.4 µl/min. Peptides were analysed with a quadrupole time-of-flight (Q-TOF) mass spectrometer (Micromass, Wythenshawe, England). A 2700 V tension was applied on the nanoelectrospray capillary (New Objective, Woburn, Mass., USA). Argon was used as collision gas. The collision energy was settled as a function of the precursor ion mass. MS/MS spectra were acquired by automatic switching between MS and MS/MS mode. Acquired MS/MS data were converted in a compatible format (DTA files) by ProteinLynx software (Micromass, Wythenshawe, England) and analysed using conventional search engines against SWISS-PROT, TrEMBL, NCBInr and EST databases. In cases of manual interpretation of MS/MS data, identification was performed by sequence only search.

It was found that marker M5 was a fragment of Cystatin C, markers M3 and M4 were isoforms of beta-2-microglobulin and M2 was a new variant or homologue of myoglobin. Marker M1 was found to be a fragment of the neurosecretory protein VGF.

Example 9

Statistical Analysis

P-values were calculated using standard statistical methods known to the person skilled in the art. P-values smaller than 0.05 were considered to be statistically significant.

Example 10

Isolation of the 4.8 kDa Fragment (Marker M1)

Some CSF samples from control patients were fractionated by Centricon 30 filtration device (Millipore Corp., Bedford, Mass.) in order to remove the protein with a molecular weight higher than 30 kDa. The salt and polypeptide with a molecular weight lower than 3 kDa were removed using a Centricon 3 (Millipore Corp., Bedford, Mass.). The Centricon 3 was then washed with ultrapure distilled water. In that wash fraction, the 4.82 kDa was found to be the major component. This liquid fraction was first reduced with a 10 mM solution of 1,4-Dithioerythritol for 1 h at 56° C., then alkylated with 54 mM iodoacetamide for 45 min at room temperature. Finally, the polypeptide was digested with 6 mg/l trypsin overnight at 37° C. This liquid fraction was analysed by nanoLC and Q-TOF as previously described.

Example 11

Different Surface Materials for SELDI-TOF Analysis

Using SELDI-TOF, an analysis of 10 CSF samples from AD patients and 10 controls was performed on three different surfaces: the hydrophobic H50, the WCX2, and the IMAC surface (Ciphergen Biosystems, Fremont, Calif., USA, resp). Seven differentially expressed peaks were found on the H50, five markers on the WCX2, and five markers on the IMAC surface. A diagnostic test using the markers on the H50 chip revealed a specificity and sensitivity of 100% and 70%, respectively. The combination of the markers found on H50 and WCX2 gave a specificity and sensitivity of 100% and 80%. Finally, the combination of the markers found on H50, WCX2 and IMAC gave a specificity and sensitivity of 100% and 90%.

The average masses of the differentially expressed polypeptides as determined by SELDI-TOF using different surface materials were as follows:
Surface hydrophobic H50: 7 peaks
Marker 1: 4769±s.d. Da
Marker 2: 6958±s.d. Da
Marker 3: 6991±s.d. Da
Marker 4: 13412±s.d. Da
Marker 5: 13787±s.d. Da
Marker 6: 17276±s.d. Da
Marker 7: 40437±s.d. Da
Surface IMAC Cu: 5 peaks
Marker 1: 6895±s.d. Da
Marker 2: 6928±s.d. Da
Marker 3: 7691 E s.d. Da
Marker 4: 7769±s.d. Da
Marker 5: 7934±s.d. Da
Surface WCX2: 5 peaks Marker 1: 5082 s.d. Da
Marker 2: 6267±s.d. Da
Marker 3: 6518±s.d. Da
Marker 4: 7274±s.d. Da
Marker 5: 8209±s.d. Da The standard deviation (s.d) is 20 Da for each marker above. However, the standard deviation can also be 40 Da, or 10 Da, or 5 Da for each marker above.

BIBLIOGRAPHY

Adam, B. L. et al. 2001, Proteomics 1(10): 1264-1270

Asgeirsson B, Haebel S, Thorsteinsson L, Helgason E, Gudmundsson K O, Gudmundsson G, Roepstorff P. Hereditary cystatin C amyloid angiopathy: monitoring the presence of the Leu68Gln cystatin C variant in cerebrospinal fluid and monocyte cultures by MS. Biochem S. 1998, 329, 497-503.

Beyer K, Lao J I, Gomez M, Riutort N, Latorre P, Mate J L, Ariza A. Alzheimer's disease and the cystatin C gene polymorphism: an association study. Neuroscience letters. 2001, 315, 17-20.

Cam N, Possenti R, Ricco A S, Rocchi M, Levi A. Cloning, structural organization analysis, and chromosomal assignment of the human gene for the neurosecretory protein VGF. Genomics 1997, 45 (2), 443-446.

Cohen D H, Feiner H, Jenson O, Frangione B. Amyloid fibril in hereditary cerebral hemorrhage with amyloidosis (HCHWA-I) is related to the gastroentero-pancreatic neuroendocrine protein. J. Exp. Med. 1983, 158, 623-628.

Current Protocols in Immunology, Eds. Coligan J E, Kruisbeek A M, Margulies D H, Shevach E M, and Strober W., John Wiley & Sons Inc. 1991

Crawford U, Freeman M I, Schinka I A, Abdullah L I, Gold M, Hartmarx R, Krivian K, Morris M D, Richards D, Duara R, Anand R, Mullan M J. A polymorphism in the cystatin C gene is a novel risk factor for late-onset Alzheimer's disease. Neurology. 2000, 55, 763-768.

Davies, H. A. 2000. The ProteinChip® System from Ciphergen: A new technique for rapid, micro-scale protein biology. J. Molecular Medicine, 78 (7):B29 Deng A, Irizarry M C, Nitsch R M, Growdon J H, Rebeck G W. Elevation of Cystatin C in susceptible neurons in Alzheimer's disease. Am. J. Pathol. 2001, 159, 1061-1068.

Emerudh J, Olsson T, Berlin G, von Schenck H. Cerebrospinal fluid immunoglobulins and beta 2-microglobulin in lymphoproliferative and other neoplastic diseases of the central nervous system. Arch Neurol. 1987, 44(9), 915-20.

Finckh U, Von der Kammer H, Velden J, Michel T, Andresen B, Deng A, Zhang J, Muller-Thomsen T, Zuchowski K, Menzer G, Mann U, Papassotiropoulos A, Heun R, Zurdel J, Holst F, benussi L, Stoppe G, Reiss J, Miserez A R, Staehelin B B, Rebeck W, Hyman B T, Binetti G, Hock C, Growdon M, Nitsch R M. Genetic association of a cystatin C gene polymorphism with late-onset Alzheimer's disease. Arch Neurol. 2000, 57, 1579-1583.

Francis, P. T. et al. I. Neurol. Neurosurg. Psychiatry 1999, 66(2): 137-147 Fung, E T et al. Protein biochips for differential profiling. Current Opinion in Biotechnology, 2001, 12(1): 65-69

Ghiso J, Jensson O, Frangione B. Amyloid fibrils in hereditary cerebral hemorrhage with amyloidosis of Icelandic type is a variant of gamma-trace basic protein (cystatin C). Proc Natl Acad Sci USA. 1986; 83(9):2974-8.

Ghiso J, Pons-Estel B, Frangione B. Hereditary cerebral amyloid angiopathy: the amyloid fibrils contain a protein which is a variant of cystatin C, an inhibitor of lysosomal cysteine proteases. Biochem Biophys Res Commun. 1986; 136(2): 548-54.

Gras R, Müller M, Gasteiger E, Gay S, Binz P A, Bienvenut W V, Hoogland C, Sanchez J C, Bairoch A, Hochstrasser D F, Appel R. Improving protein identification from peptide mass fingerprinting through a parameterised multi-level scoring algorithm and an optimised peak detection. Electrophoresis 1999, 20: 3535-3550

Grubb A O, Jensson O, Gudmundsson G, Amason A, Lofberg H, Maim I. Abnormal metabolism of g-trace alkaline microprotein. The basic defect in hereditary cerebral hemorrhage with amyloidosis. N Engl. J. Med 1984, 311, 1547-1549.

Hellman U, Wernstedt C, Góñez, J, Heldin C H. Improvement of an "In-Gel" digestion procedure for the micropreparation of internal protein fragments for amino acid sequencing. Anal. Biochem. 1995, 224, 451-5.

Hoekman K, Van Nieuwkoop J A, Willemze R. The significance of beta-2 microglobulin in clinical medicine. Neth J Med. 1985; 28(12):551-7.

Huse W D, Sastry L, Iverson S A, Kang A S, Alting-Mees M, Burton D R, Benkovic S J, Lerner R A. Generation of a large combinatorial library of the immunoglobulin repertoire in phage lambda. 1989, Science 246: 1275-1281.

Issaq H J, Veenstra T D, Conrads T P, Felschow D. The SELDI-TOF MS approach to proteomics: protein profiling and biomarker identification. Biochem. Biophys. Res. Commun. 2002, 292 (3): 587-592

Kalman J, Marki-Zay J, Juhasz A, Santha A, Dux L, Janka Z. Serum and Cerebrospinal fluid cystatin C levels in vascular and Alzheimer's dementia. Acta Neurol. Scand. 2000, 101, 279-282.

Laemmli U K. Cleavage of structural proteins during the assembly of the head of bacteriophage T4. Nature. 1970 Aug. 15; 227(259):680-5.

Leung-Tack J, Tavera C, Gensac M C, Martinez J, Colle A. Modulation of phagocytosis-associated respiratory burst by human cystatin C: role of the N-terminal tetrapeptide Lys-Pro-Pro-Arg, Exp. Cell Research. 1990, 188, 16-22.

Levy E, Sastre M, Kumar A, Gallo G, Piccardo P, Ghetti B, Tagliavini F, Codeposition of cystatin C with amyloid-beta protein in the brain of Alzheimer's disease patients. J. Neuropathol Exp Neurol 2001, 60, 94-104

Merchant M, Weinberger S R. Recent advancements in surface-enhanced laser desorption/ionization-time of flight-mass spectrometry. Electrophoresis, 2000, 21: 1164-1167

Popovic T, Brzin J, Ritonja A, Turk V. Different forms of human Cystatin C. Biol. Chem. Hoppe-Seyler. 1990, 371, 575-580.

Raymackers J, Daniels A, DeBrabandere V, Missiaen C, Dauwe M, Verhaert P, Vanmechelen E, Meheus L. Identification of two dimensionally separated human cerebrospinal fluid proteins by N-terminal sequencing, matrix-assisted laser-desorption/ionization-mass spectrometry, nanoliquid chromatography-electrospray ionization-time of flight-mass spectrometry, and tandem mass spectrometry. Electrophoresis, 2000, 21, 2266-2283.

The Ronald and Nancy Reagan Research Institue of the Alzheimer's Association and the National Institute on Aging Working Group. Consensus Report of the Working Group on: "Molecular and Biochemical Markers of Alzheimer's Disease". Neurobiology of Aging, 1988, 19 (2): 109-116.

Robles A. Some Remarks on biological markers of Alzheimer's Disease. Neurobiology of Aging, 1998, 19 (2): 153-157

Rosenfeld J, Capdevielle J, Guillemot J C, Ferrara P. In-gel digestion of proteins for internal sequence analysis after one- or two-dimensional gel electrophoresis. *Anal. Biochem.* 1992, 203, 173-9.

Shevchenko A, Wilm M, Vorm O, Mann M. Mass spectrometric sequencing of proteins silver-stained polyacrylamide gels. *Anal. Chem.* 1996, 68, 850-8.

Teunissen C E, de Vente J, Steinbusch H W M, De Bruijn C. *Neurobiology of Aging,* 2002, 23: 485-508

U.S. Pat. No. 4,366,241

U.S. Pat. No. 4,376,110

U.S. Pat. No. 4,517,288

U.S. Pat. No. 4,837,168

Ward E S et al., Binding activities of a repertoire of single immunoglobulin variable domains secreted from *Escherichia coli*. Nature 1989, 341, 544-546

Wei L, Delman Y, Castano E M, Cadene M, Beavis R C, Devi L, Levy E. Instability of the amyloidogenic cystatin. C variant of hereditary cerebral hemorrhage with amyloidosis, Icelandic type. *J. Biol. Chem.,* 1998, 273, 11806-11814.

Wulfkuhle J D, McLean K C, Paweletz C P, Sgroi D C, Trock B J, Steeg P S, Petricoin E F. New approaches to proteomic analysis of breast cancer. *Proteomics* 2001, 1 (10): 1205-1215

Xiao Z, Adam B L, Cazares L H, Clements M A, Davis J W, Schellhammer P F, Dalmasso E A, Wright G L. Quantitation of serum prostate-specific membrane antigen by a novel protein biochip immunoassay discriminates benign from malignant prostate disease. 2001, *Cancer Research* 61 (16): 6029-6033

The invention claimed is:

1. A method for assessing the state of Alzheimer's disease in a subject, wherein the method comprises detecting in a sample from the subject at least five distinct polypeptides meeting the following criteria:
  a first polypeptide having the amino acid sequence of SEQ ID NO: 17;
  a second polypeptide having the amino acid sequence of SEQ ID NO: 1 or 2;
  a third polypeptide having the amino acid sequence of SEQ ID NO: 3;
  a fourth polypeptide having the amino acid sequence of SEQ ID NO: 4, 5, or 6; and
  a fifth polypeptide having the amino acid sequence selected from the group consisting of SEQ ID NO: 7 to SEQ ID NO: 16.

2. The method of claim 1, wherein the method further comprises contacting the sample with an antibody that specifically binds to one of the at least five polypeptides.

3. The method of claim 1, wherein one or more of the at least five polypeptides is detected by SELDI-TOF MS.

4. The method of claim 1, wherein the method is performed on at least two samples from the subject.

5. The method of claim 1, wherein the sample is CSF, blood, serum, plasma, urine, seminal plasma, nipple fluid, or cell extract.

* * * * *